United States Patent
Hoult

Patent Number: 5,877,435
Date of Patent: Mar. 2, 1999

[54] CARRIER AND ITS USE IN THE PREPARATION OF SAMPLES FOR SPECTROSCOPY

[75] Inventor: Robert A. Hoult, Beaconsfield, United Kingdom

[73] Assignee: Perkin-Elmer Ltd., Beaconsfield, England

[21] Appl. No.: 892,780

[22] Filed: Jul. 15, 1997

[30] Foreign Application Priority Data

Jul. 16, 1996 [GB] United Kingdom .................... 9614961

[51] Int. Cl.$^6$ ...................................................... G01N 1/04
[52] U.S. Cl. ........................................................ 73/864.41
[58] Field of Search ........................... 73/864.41, 864.81; 356/36, 244; 451/523, 540, 548, 551, 57, 552, 553

[56] References Cited

U.S. PATENT DOCUMENTS

| | | | |
|---|---|---|---|
| H901 | 3/1991 | Eckart et al. ............................ | 250/304 |
| 5,363,601 | 11/1994 | Baltazar et al. ......................... | 451/548 |
| 5,423,719 | 6/1995 | Jennings ................................. | 451/540 |
| 5,703,681 | 12/1997 | Hoult ....................................... | 356/36 |

FOREIGN PATENT DOCUMENTS

| | | |
|---|---|---|
| 4443885 | 11/1985 | Australia . |
| 2280133 | 1/1995 | United Kingdom . |

OTHER PUBLICATIONS

Stuhlinger T. W. et al.: "Bidirectional Reflectance Distribution Function of Gold–Plated Sandpaper"—Applied Optics, vol. 20, No. 15, 1 Aug. 1981, pp. 2648–2655.

Spragg R. A.: "A Rapid Sample Preparation Technique For Diffuse Reflectance Measurements", Applied Spectroscopy, vol. 38, No. 4, 1 Jul. 1984, pp. 604–605.

*Primary Examiner*—Robert Raevis
*Attorney, Agent, or Firm*—David Aker

[57] ABSTRACT

A carrier for use in the preparation of samples for spectroscopic analysis comprises a rod-like element 10 housing a domed end 11. The dome end 11 is coated with abrasive material. To prepare a sample the abrasive material is rubbed by linear movement or rotation against the material to be analysed. That material becomes abraded and attaches to the end 11. The carrier can be formed from a commercially available dowel and is therefore easy to make and use.

6 Claims, 1 Drawing Sheet

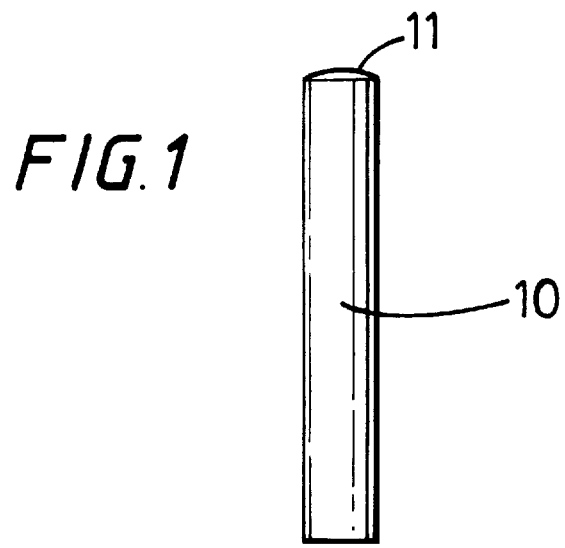
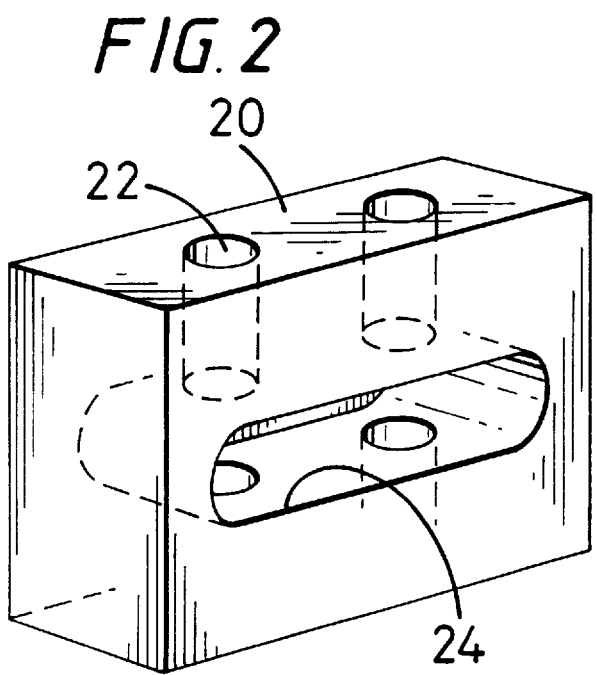

CARRIER AND ITS USE IN THE PREPARATION OF SAMPLES FOR SPECTROSCOPY

FIELD OF THE INVENTION

This invention relates to the preparation of samples for spectroscopy and in particular relates to the preparation of samples of solid materials.

BACKGROUND ART

In the field of mid infrared spectroscopy of solids a significant problem which has been encountered is the preparation of samples of the solids which are sufficiently thin to transmit significant amounts of infrared radiation in order to enable the spectroscopic analysis to take place. A known way of attempting to deal with the problem has been to abrade the solid material using a commercially available abrasive paper, e.g. sandpaper, which typically incorporates particles of SiO and $Al_sO_3$. This creates on or in the sandpaper small particles of solid material to be investigated. The sandpaper is then placed in an instrument which can be used to carry out the spectroscopic analysis and a spectrum of the sandpaper is measured in diffused reflectance in a known way. This reveals the characteristic spectrum of the sample, in particular the small particles of the sample embedded in the sandpaper.

An enhancement of this method is to use sandpaper coated with a relatively thin coating of high reflective material such as aluminium.

It has been the practice to use small discs of sandpaper for forming samples as described above. Such small discs are satisfactory when the surface of the material to be analysed has projections such as a corner against which the abrasive surface can be rubbed to form the sample on the surface of the sandpaper. However, for very flat surfaces or for surfaces where there are recesses, it can be more difficult to obtain a satisfactory sample using the sandpaper discs. The present invention has been devised in order to deal with this problem.

SUMMARY OF THE INVENTION

According to the present invention there is provided a carrier for use in the preparation of samples for spectroscopic analysis, said carrier comprising a generally rod-like element, one end face of which is generally domed and has formed thereon a layer of abrasive material.

In use of the carrier the rod-like element is held so that the abrasive material contacts the surface of the material to be analysed. By rubbing the abrasive material against the surface, a sample of the material to be analysed is formed on the end of the carrier. The rod-like element can then be located in a spectroscopic apparatus, or an accessory of such an apparatus and a spectrum of the material can be measured in diffused reflectance in a manner known to those skilled in the art.

The abrasive material is preferably coated with a highly reflective coating. The coating may be aluminium.

The rod-like element may take the form of a commercially available dowel. Such dowels are conventionally supplied with one domed end face.

An advantage of the present invention is that it facilitates obtaining samples from very flat or recessed surfaces. The domed end face is particularly effective in obtaining samples from such a surface since it enables the carrier to be held in a manner which provides sufficient pressure to abrade the surface of the material, whilst maintaining control over the rod-like element.

BRIEF DESCRIPTION OF THE DRAWINGS

The invention will be described now by way of example only, with particular reference to the accompanying drawings. In the drawings:

FIG. 1 is a side elevation of a carrier in accordance with the present invention, and FIG. 2 is a perspective view showing a holder for the carrier, which holder can be located in an accessory of a spectroscopic instrument.

DETAILED DESCRIPTION OF THE PREFERRED EMBODIMENT

Referring to FIG. 1, a carrier for use in spectroscopic analysis comprises a commercially available dowel (10), one end face (11) of which is slightly domed. This end face has been coated with a layer of abrasive material such as abrasive grit and the layer of abrasive material has further been coated with a coating of highly reflective material such as aluminium. The layers can be formed by commercially available coating processes. In order to use the carrier to form a sample for spectroscopic analysis, the carrier is held manually and the coated end face (11) is located against a surface of the material. The dowel is manipulated either by linear movement or by rotation in such a way that material from the surface is abraded and becomes attached to the end face of the dowel. The dowel is typically of the order of 20 mm long and 3 mm in diameter and this makes it convenient to hold manually and to manipulate in order to obtain the sample as described above.

Once the sample has been obtained the dowel is located in a holder such as that shown in FIG. 2 of the drawings. This holder comprises a rectangular block (20) of plastics material into which extends at least one bore such as that shown at (22). The bore has an internal diameter corresponding to the external diameter of the dowel and the dowel (10) is located in the bore (22). The holder then is placed in a compartment in an accessory of a spectroscopic instrument, such that infrared radiation can be fed to the end face of a dowel and the sample analysed in diffused reflection in a manner known to those skilled in the art. It will be seen that the holder can have a cutaway portion (24) on one of its faces, thereby exposing an axial part of the bore (22). This arrangement facilitates removal of a dowel from the bore.

It will be appreciated that the use of a dowel of the type described above provides an effective and very inexpensive carrier for forming samples for spectroscopic analysis. After use the dowel can simply be disposed of and another suitably coated dowel used for the next sample.

I claim:

1. A method of preparing a sample of solid material for spectroscopic analysis which comprises providing a carrier comprising a generally rod-like element, one end face of which is generally domed and has formed thereon a layer of abrasive material, and abrading a solid material with the domed end face to form a layer of the material to be analyzed on the domed end face.

2. A method according to claim 1, wherein the abrasive material is coated with a highly reflective coating.

3. A method according to claim 2, wherein the rod-like element comprises a commercially available dowel.

4. A method according to claim 2, wherein the coating is aluminum.

5. A method according to claim 4, wherein the rod-like element comprises a commercially available dowel.

6. A method according to claim 1, wherein the rod-like element comprises a commercially available dowel.

* * * * *